(12) United States Patent
Gellerstedt et al.

(10) Patent No.: US 12,154,700 B2
(45) Date of Patent: Nov. 26, 2024

(54) RADIATION PROTECTIVE DEVICE

(71) Applicant: Texray AB, Gothenburg (SE)

(72) Inventors: Fredrik Gellerstedt, Kungsbacka (SE); Petra Apell, Onsala (SE)

(73) Assignee: Texray AB, Gothenburg (SE)

( * ) Notice: Subject to any disclaimer, the term of this patent is extended or adjusted under 35 U.S.C. 154(b) by 0 days.

(21) Appl. No.: 17/619,033

(22) PCT Filed: Jun. 12, 2020

(86) PCT No.: PCT/SE2020/050613
§ 371 (c)(1),
(2) Date: Dec. 14, 2021

(87) PCT Pub. No.: WO2020/251468
PCT Pub. Date: Dec. 17, 2020

(65) Prior Publication Data
US 2022/0287396 A1   Sep. 15, 2022

(30) Foreign Application Priority Data
Jun. 14, 2019 (SE) .................................. 1930192-8

(51) Int. Cl.
*G21F 3/02* (2006.01)
*A61B 6/10* (2006.01)
*A41D 13/05* (2006.01)

(52) U.S. Cl.
CPC ................ *G21F 3/02* (2013.01); *A61B 6/107* (2013.01); *A41D 13/0512* (2013.01)

(58) Field of Classification Search
CPC ........ A61B 6/107; A41D 13/0512; G21F 3/02
See application file for complete search history.

(56) References Cited

U.S. PATENT DOCUMENTS

| 1,272,336 A | * | 7/1918 | Edmonds | ................ B63C 9/115 |
| | | | | 441/123 |
| 4,386,277 A | * | 5/1983 | Forshee | .................... G21F 3/02 |
| | | | | 2/9 |

(Continued)

FOREIGN PATENT DOCUMENTS

| CN | 208447625 U | 2/2019 | |
| DE | 29712294 U1 * | 10/1997 | ............. A61B 6/107 |

(Continued)

OTHER PUBLICATIONS

Coronal. (2016). In Editors of the American Heritage Dictionaries (Ed.), The American Heritage (R) dictionary of the English language (6th ed.). Houghton Mifflin. Credo Reference: https://search.credoreference.com/content/entry/hmdictenglang/coronal/0?institutionId=743 (Year: 2016).*

(Continued)

*Primary Examiner* — Michael J Logie
(74) *Attorney, Agent, or Firm* — Downs Rachlin Martin PLLC (57) ABSTRACT

A radiation protective device, such as a thyroid collar, for protection against radiation, such as ionizing radiation is disclosed. The device comprises a first section extending in a transverse direction, from a first front portion to a first back portion, in a coronal direction, and in a sagittal direction, the first front portion and the first back portion having a length in the coronal direction, and a second section extending in the transverse direction, from a second front portion to a second back portion, in the coronal direction, and in the sagittal direction, the second front portion and the second back portion having a length in the coronal direction, wherein the second front portion of the second section is arranged at least partially coronal of the first front portion of the first section.

20 Claims, 4 Drawing Sheets

(56) References Cited

U.S. PATENT DOCUMENTS

| | | | | |
|---|---|---|---|---|
| 5,083,319 | A * | 1/1992 | Grilliot | A41D 27/18 |
| | | | | 2/81 |
| 5,500,954 | A * | 3/1996 | Smith | A41D 13/11 |
| | | | | 2/9 |
| 5,523,581 | A | 6/1996 | Cadwalader | |
| 2007/0138415 | A1 * | 6/2007 | Rees | A61B 6/107 |
| | | | | 250/516.1 |
| 2009/0184269 | A1 * | 7/2009 | Rees | A61B 6/107 |
| | | | | 250/516.1 |
| 2013/0219601 | A1 * | 8/2013 | Shafer | A61B 6/542 |
| | | | | 2/468 |
| 2014/0054474 | A1 | 2/2014 | Rees | |
| 2014/0117288 | A1 * | 5/2014 | Rebar | G21F 3/025 |
| | | | | 250/516.1 |
| 2014/0367594 | A1 | 12/2014 | Reynolds | |
| 2018/0042314 | A1 * | 2/2018 | Morisch Hurst | A41D 27/16 |
| 2019/0336088 | A1 * | 11/2019 | Gordon | A61B 6/10 |

FOREIGN PATENT DOCUMENTS

| | | | |
|---|---|---|---|
| JP | 2001296391 | A | 10/2001 |
| KR | 20180097074 | A | 8/2018 |
| KR | 20190047242 | A | 5/2019 |
| WO | 2013128240 | A1 | 9/2013 |
| WO | 2018152331 | A1 | 8/2018 |

OTHER PUBLICATIONS

KR-20150009812-A and machine translation obtained from FIT (Year: 2015).*
Haddad et al., "Chin-throat anatomy: Normal relations and changes following orthognathic surgery and growth modification", Angle orthodontist, 2017 (Year: 2017).*
Naini et al., "Submetal Cervical angle: perceived attractiveness and threshold values of desire for surgery", Oral Sug., 2016 (Year: 2016).*
DE-29712294-U1—machine translation (Year: 2023).*
JP2008538136 machine translation (Year: 2008).*
Merriam-Webster (Ed.). (2016). Chin. In Merriam-Websteras Medical Dictionary (1st ed.). Merriam-Webster. https://search.credoreference.com/articles/Qm9va0FydGljbGU6NDE2OTI2NA==? aid=279753 (Year: 2016).*
International Search Report and Written Opinion dated Sep. 1, 2020, in connection with PCT/SE2020/050613, filed Jun. 12, 2020.

* cited by examiner

RADIATION PROTECTIVE DEVICE

FIELD OF THE INVENTION

This invention pertains in general to the field of radiation protective devices for protection against ionizing radiation, particular for use in medical interventions. More particularly, the invention relates to a radiation protective device, such as a thyroid collar, for protection against radiation, such as ionizing radiation is disclosed. The device comprises a first section extending in a transverse direction, from a first front portion to a first back portion, in a coronal direction, and in a sagittal direction, the first front portion and the first back portion having a length in the coronal direction, and a second section extending in the transverse direction, from a second front portion to a second back portion, in the coronal direction, and in the sagittal direction, the second front portion and the second back portion having a length in the coronal direction, wherein the second front portion of the second section is arranged at least partially coronal of the first front portion of the first section.

BACKGROUND OF THE INVENTION

In surgical procedures where ionizing radiation, such as X-ray, is used continuously, the surgical staff needs to protect themselves from the emitted radiation. Emitted radiation can be direct exposure as well as scatter radiation. Therefore, radiation protective garments, such as an apron together with a thyroid collar and sometimes also lead containing eye glasses, are used to protect against the radiation. This will cover approximately 75% of the body but not lower legs, arms or cranium.

Other products that may be used by the surgeon are a radiation protective cap and lead containing glass screens. If no protection is used, the surgeon will be induced to an accumulating lethal dose of radiation over time.

The radiation dose is cumulative. Thus, stochastic effects can be a major threat to medical staff involved in interventional procedures. The harmful biological effects of ionizing radiation on the thyroid gland is well known. It is therefore necessary to strive to reduce radiation exposure and the amount of scatter radiation. A thyroid shield is an effective way to minimize the radiation exposure during procedures. A thyroid collar is a standard shield for interventional medical staff. A thyroid collar is typically designed to cover the part of the throat where the thyroid gland is, resulting in a design illustrated in FIG. 1. This results in a reduction of scatter radiation towards the thyroid gland. However, a thyroid collar does not reduce the amount of radiation inside the skull. When scatter radiation is radiated from the patient and up towards the operator, the radiation that hits the thyroid collar or other shields is minimized. However, scatter beams that do not hit shields continue through the skull and the brain.

During surgery, the surgeon typically runs an energy source, such as an X-ray source, monitoring intermittently by a foot pedal. An X-ray beam is then emitted from the energy source that is placed either over or under the patient. On the opposed side of the patient is a radiation detection device situated where the X-ray image is digitally processed for presentation on monitors next to the surgeon.

The primary electrons that is emitted from the energy source hits the patient whereby some electrons will pass through the patient thus creating the X-ray image. Other electrons will either be absorbed by the tissue and fat from the patient or scattered from the patient as secondary electrons. The latter energy source will be a substantial part of the radiation that the surgical staff needs to protect themselves from. Hence, a majority of the harmful radiation comes towards the staff as secondary radiation from underneath (the patient).

The surgical staff uses radiation protective apron to cover internal organs in the torso, scrotum and thigh area. The thyroid collar protects the thyroidea and neck. Lead supported eye glasses protects the eyes from radiation and also some part of the brain. Radiation protective caps also protect the cranium and brain from other angles than from the patient. Hence, the cranium of the surgeon is still to a large extent unprotected from radiation scattered from the patient.

The radiation dose decreases exponentially with the length from the energy source (i.e. the patient) which means that it is more important to protect organs closer to the patient, however the dose that reach the eye level of the staff is measured to 0.5 Gy which is over the threshold for circulatory diseases.

Hence, an improved protection from ionizing radiation, such as X-ray, towards the skull and brain during a medical intervention would be advantageous and in particular allowing for improved precision, increased flexibility, increased comport, cost-effectiveness, and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing embodiments of a radiation protective device according to embodiments of the invention.

According to a first aspect of the invention, a radiation protective device, such as a thyroid collar, for protection against radiation, such as ionizing radiation, comprises a first section extending in a transverse direction, from a first front portion to a first back portion, in a coronal direction, and in a sagittal direction, the first front portion and the first back portion having a length in the coronal direction, and a second section extends in the transverse direction, from a second front portion to a second back portion, in the coronal direction, and in the sagittal direction, the second front portion and the second back portion having a length in the coronal direction, wherein the second front portion of the second section is arranged at least partially coronal of the first front portion of the first section.

The second section may be angled in the coronal direction relative the first section.

The second portion has a top end that may be curved from a front towards a back thereof.

A height of the second portion may be higher at the front than at the back.

According to another embodiment, the protective device comprises a panel that may comprise a fastening mechanism, such as hooks and/or loops, tape or any other mechanism that may attach two objects to each other reversibly or irreversibly, and wherein the panel is curved to extend around the neck of a user when attached to another radiation protective device, such as an apron and/or a thyroid collar and to extend coronally of the other radiation protective device when attached thereto.

Further embodiments of the invention are defined in the dependent claims.

Some embodiments of the invention provide for improved radiation protection of the skull and brain of a wearer.

Furthermore, the invention provides embodiments wherein a radiation protective device is efficient at the same time as being comfortable to wear.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 2b is a schematic side view of an embodiment of the protective device according to the invention as illustrated in FIG. 2a;

FIG. 2c is a schematic top view of an embodiment of the protective device according to the invention as illustrated in FIG. 2a;

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable as a radiation protective garment for medical procedures. However, it will be appreciated that the invention is not limited to this application but may be applied to many other procedures, such as other areas where a radiation protective garment may be used.

The invention will be described in the form of a thyroid collar as an example of a protective device for illustrative purposes. However, the invention is not limited to a thyroid collar but can be adapted to as a panel that can be attached to a thyroid collar or other protective devices such as an apron. The protective device has an extension to protect the skull and brain during use. Use together with a thyroid collar is one such example.

Figure 1:
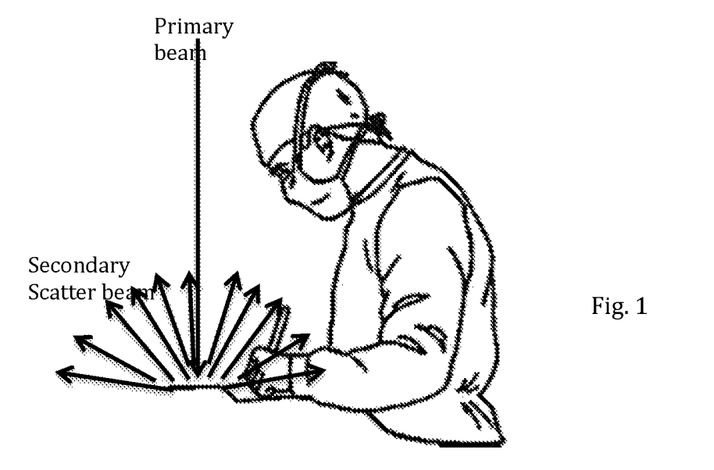
FIG. 1 is a schematic view of an operator wearing an apron, primary radiation, and secondary radiation during a surgical intervention.

Embodiments of the invention relates to a protective device, such as thyroid collar that has an extended panel that reaches out from the upper section of the thyroid collar. This panel may extend out from the collar as to form a shied under the user's chin in order to block scattered radiation that is angled, such as illustrated in FIG. 1. For example, the panel may extend out from the collar as to form a shield under the users chin in order to reduce scatter radiation coming from oblique below. In an embodiment, a radiation protective device has a first section and a second section, wherein the first section is positioned around the user's neck and the second section extends from the first section. In this example embodiment, the second section has a front portion that is configured with sufficient size to position an edge at and in front of the user's face between the chin and mouth, wherein the edge is an upper and outer terminal edge of the radiation protective device.

Figure 2A:
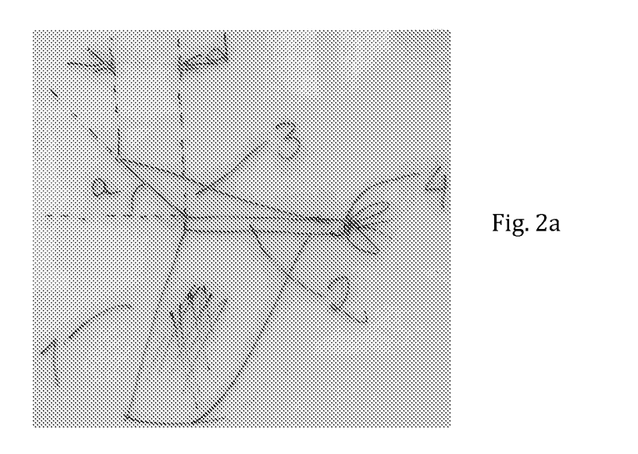
FIG. 2a is a schematic view of an embodiment of the protective device according to the invention.
Figure 2B:
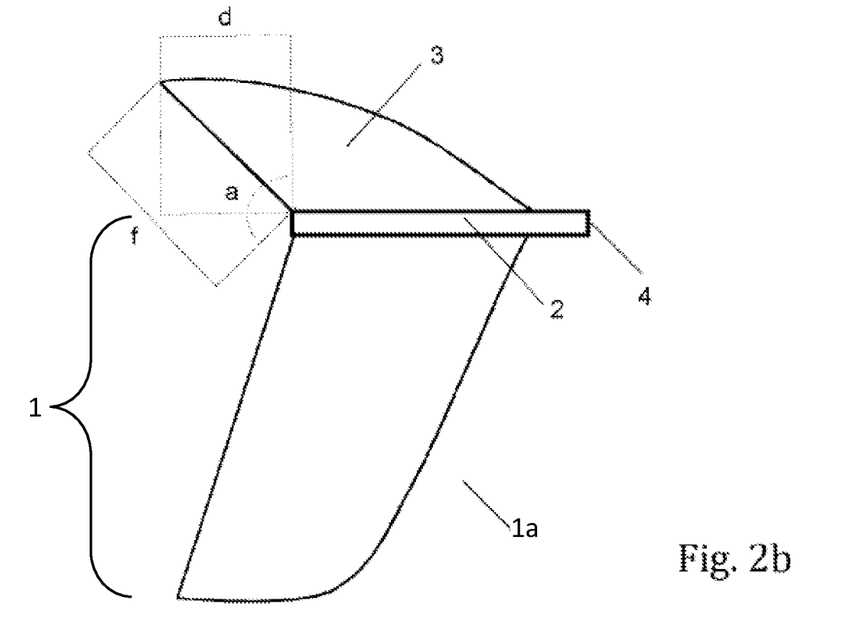
Figure 2C:
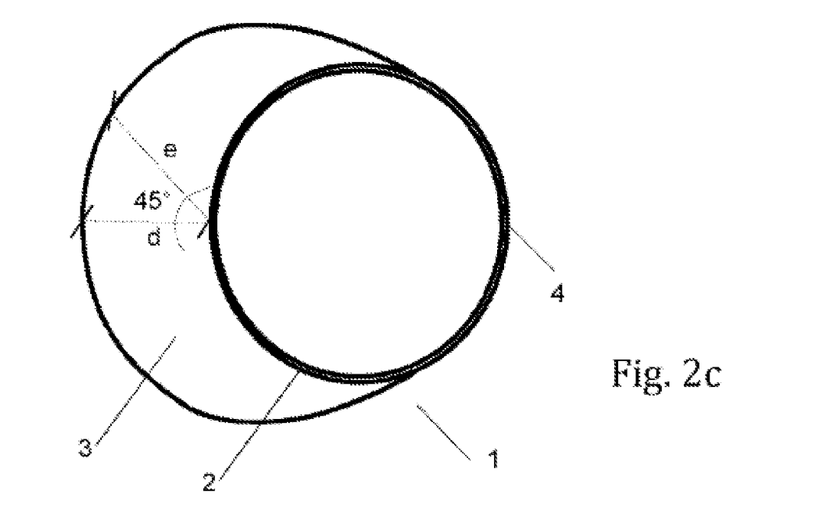

Embodiments of the invention are illustrated in FIGS. 2A-2C. The thyroid collar 1 has a purpose to protect the thyroidea and neck region of the user. By increasing the height of the front line 2 of the thyroid collar, more of the user will be protected by a further reduction of radiation exposure, especially the larynx region, included section A, and sections B-D (see FIG. 6). However, conventional thyroid collars are not designed in this manner because their single purposes are to protect the thyroidea. Another reason for not increasing the height of the front line as described is because of the reduction of movement capability and discomfort. Still other reasons for not increasing the height is that it may restrain the user's visual field as well as impaired breathing.

According to embodiments as illustrated in FIGS. 2a-2c, an extending panel 3 may be added to a thyroid collar, where said panel 3 is positioned in an angle a from the collar so that the surface of said panel is directed away from at least a portion of the collar a distance d. This shields the cranium from scatter radiation coming from below. The distance d, extending in line with forward or sidewise looking eyes, may preferably be greater than 15 mm. In some embodiments, the distance d is greater than 30 mm. In some embodiments, the distance d is greater than 40 mm. Such embodiments can provide an active cranial shield for radiation reduction, and the maximum distance of d is determined by the comfort, movement, and visual field of the user. In some embodiments the distance d does not extend more than 150 mm from the front line of the thyroid collar 1. In other embodiments, the distance d does not extend more than 130 mm from the front line of the thyroid collar 1. In other embodiments, the distance d does not extend more than 100 mm from the front line of the thyroid collar 2. In still other embodiments, the distance d does not extend more than 60 mm from the front line of the thyroid collar 2. Distance e, measured in a 45 degree angle from the forward looking eye of the user, shall, preferably, on the left and right hand side extend equally long. Alternatively, the distance e, measured in a 45 degree angle from the forward looking eye of the user on the left and right hand side extends different distances. Distance e and distance d are calculated from a position where the thyroid collar 1 meets the extended panel 3, such at the front line. Distance e and distance d are calculated to the opposing outer edge of the extended panel 3. The forward looking eye of the user is exemplified in FIGS. 2a-2c at a centerline between the eyes of the user. In other embodiments, the distance e is measure in other angles, such as an angle in the range of 45-90 degrees. Preferably, distance e (see FIG. 2c) is measured in a 45 degree angle from the forward looking eye of the user extends not less than 10%, more preferably not less than 30%, even more preferably not less than 50% of the forward going distance d. For example, the distance e on the right side can extend about 50-90% of distance e on the left side when measured in a 45 degree angle from the forward looking eye of the user, or vice versa. The distance e, measured in a 45 degree angle from the forward looking eye on the left and/or right hand side of the user may also be greater than the distance d but not more than about 160%-200% of the forward going distance d. The angle a is relevant for the optimization of the shielding surface. In some embodiments, the angle a is less than 89 degrees, and preferably less than 75 degrees. In other embodiments, the angle a of the extending panel is larger than −45 degrees. If the angle a is smaller, the efficiency may be too low. Hence the angle a should be higher than −45 degrees, preferably higher than −20 degrees, more preferably over 0 degrees. The total surface of the panel 3 should be as large as possible without impairing the user's vision or movability. As illustrated in FIG. 2b, distance f, measured from the frontline of thyroid collar 2 to the sagittal edge of the extended panel 3 is in some embodiments not longer than 150 mm, more preferably not longer than 120 mm, more preferably not longer than 80 mm. However, in order to be an efficient protection, the distance f is in some embodiments longer than 15 mm, more preferably longer than 20 mm, more preferably longer than 30 mm. In some embodiments the distance f is longer than 15 mm and not longer than 80 mm. In other embodiments, the distance f is longer than 30 mm and not longer than 120 mm. A closure 4 is shown in FIG. 2A. Other embodiments are foreseeable.

In some embodiments, the radiation protective panels or material in the device 1a may consist of a highly filled composition of one or several metals. Such panel(s) being constituted by one or several layers of metal combinations. In other embodiments, such panel(s) may also be constituted by a homogeneous casted film or as a radiation protective fibrous material having its filaments placed in a regular or irregular pattern.

The panel 3 may also be separate from the thyroid collar 1 and attached to the collar by a fastening mechanism in a manner to achieve a complete device 1a or to extend or complement the collar to achieve the desired protection of the skull and brain.

Embodiments of the invention provide an extra shield for scatter radiation that is currently transmitted from the patient and that do not hit protective shields. By improving the thyroid collar with an extending panel, a larger amount of scatter radiation towards the head can be reduced. Consequently, the radiation dose inside the brain is lower for medical staff wearing the invention than for medical staff that only use a conventional thyroid collar. This is illustrated in FIG. 3a (conventional thyroid collar) and FIG. 3b (embodiment of invention).

Figures 3A, 3B:
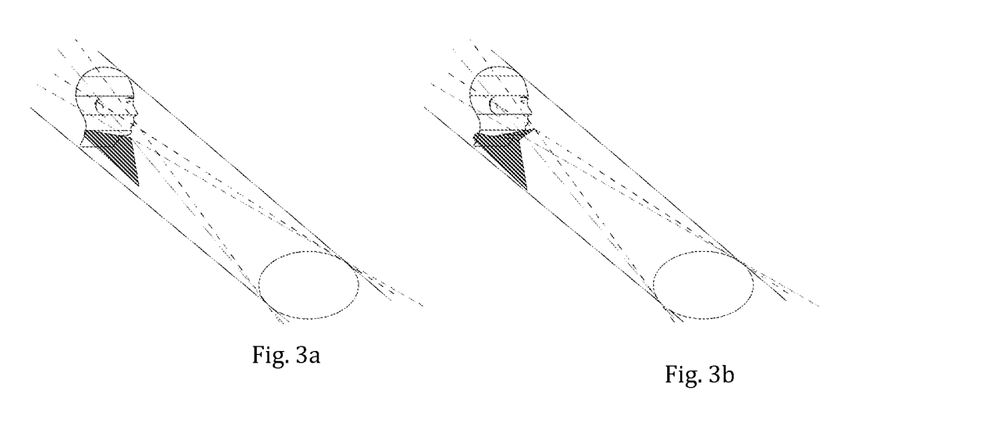
FIG. 3a is a schematic picture of a wearer of a thyroid collar according to the prior art. The picture also illustrates the angle for where most secondary radiation exposes the user.
FIG. 3b is a schematic picture of a thyroid collar having an extended front panel according to embodiments of the invention. The picture also illustrates the angle from where the majority of secondary radiation exposes the user, as illustrated in FIG. 1.

FIG. 3b illustrates the geometric connection between radiation exposure to the brain and the design of the thyroid collar where the panel 3 acts as to protect the wearer from secondary radiation coming from the patient.

By increasing the active radiation protection surface towards the user as illustrated in FIG. 3b, the thyroid collar will, in addition, be active also towards the cranial area thus partially protecting the brain from secondary radiation coming from the patient, thus reducing the risk of brain injuries and diseases originated from excessive radiation exposure.

Lab studies have shown that the cranium has a significant reduction in radiation exposure using a product designed according to FIG. 3b, as illustrated in the examples below. The studies show that radiation exposure towards the lower and middle sections of the head is reduced.

Example 1

Figure 4:
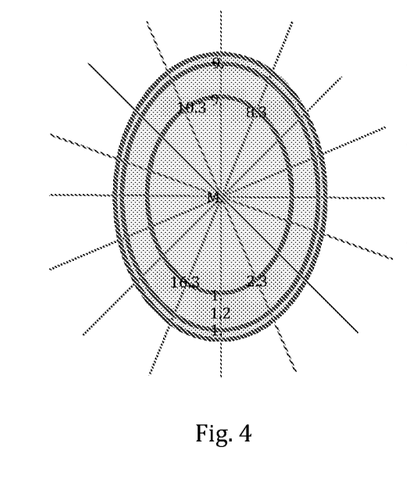
FIGS. 4 and 5 are cross-sectional views of a section of the head, with an aid for the location of the dosimeter probes as described in Examples 1 to 4.
Figure 5:
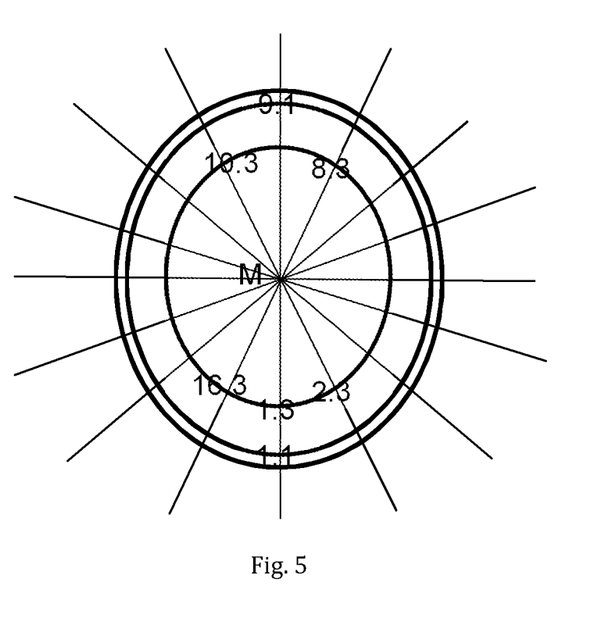

Measuring radiation exposure by using a phantom, illustrated in FIGS. 4 and 5, helps to illustrate the benefits of the extension panel 3 where 1.1 denotes the front of the head and 16.3 the back of the head. Dosimeters were placed according to scheme in FIGS. 4 and 5 in a cross section of Throat, Chin, Ear, Brain and Scalp (illustrated by sections A (Throat), B (Chin), C (Ear), D (Brain) and E (Scalp) in FIG. 6). The exposure time was 20 minutes whereafter the dose was read. Table 1 below illustrates the radiation exposure for a user wearing an ordinary radiation protection according to FIG. 3a.

The X-ray equipment used during the measurements was Philips Multi Diagnost Eleva FD (Koninklijke Philips Electronics N.V). The the patient-table were set at zero-degree angle, and a under table X-ray tube position was used with no rotation. Furthermore, the zoom format was 48 cm, using a field size of 30*30 cm, with a source image distance (SID) of 125 cm. The system was set in image-mode, at 2 frames per second, with the beam quality, tube voltage 93 kV, tube current 25 mAs and filtered with 1 mm Al plus 0.1 mm Cu. Thermoluminescent dosimeters (TLD) was used in the measurements, DXT-RAD Ringlets TLD-100, HARSHAW TLD 6600 PLUS Thermo Scientific, USA. It is a lithium fluoride crystal dosimeter (LiF: Mg, Ti), with a sensitivity range between 10 μGy to 1 Gy. To simulate the interventionist, an anthropomorphic phantom was used (Rando Alderson, CA, USA) (head, torso, abdomen and hip) which was placed perpendicular to the X-ray equipment table. An anthropomorphic abdominal pelvis phantom was used as a patient and centered on the table. The interventionist phantom was placed beside the table, in front of the patient phantom, where the X-ray tube's central beam entered the patient phantom, 50 cm perpendicular from the center of the patient phantom. In all measurements, RaySafes (Unfors RaySafe AB, Billdal, Sweden) i3 dosimeter, and the X-ray equipment's transmission ionization meter, measuring the Kerma Area Product, were used to indicate that the amount of scattered radiation that entered the interventionist phantom was equal in all the different measuring situations.

Figure 6:
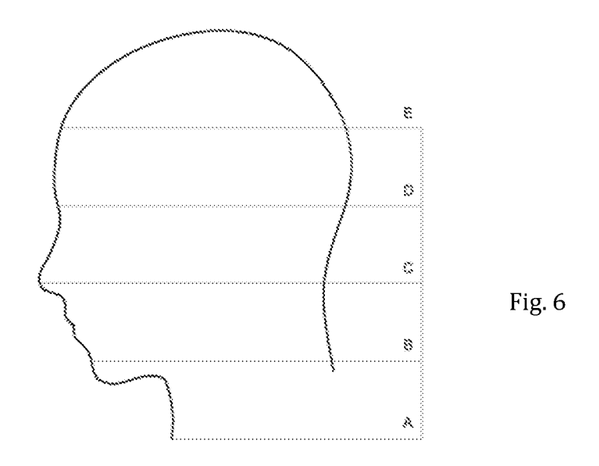
FIG. 6 is a side view of a users head with sections A-E indicated.

Table 1 below illustrates the quotient between the radiation exposures for a user wearing the ordinary thyroid collar, according to Example 1, compared to not having any protection according to the set-up of Example 1. The values in Table 1 are the quotients in each position, as illustrated in FIGS. 4 and 5, in sections A-E, as illustrated in FIG. 6. Quotients of 1.0 and above indicates that no decrease in radiation was measured, whereas quotiens below 0 indicates that 100% radiation decrease was measured. Quotients inbetween 0 and 1 indicates a radiation decrease corresponding to the indicated value.

TABLE 1

| E Quotient | D Quotient | C Quotient | B Quotient | A Quotient |
|---|---|---|---|---|
| 1.1 | 0.8 | 0.7 | 0.9 | 0.1 | 1.2 |
| 9.1 | 1.8 | 0.3 | 0.8 | 7.7 | 0.2 |
| 1.2 | 1.0 | 1.0 | 0.6 | 0.1 | 1.6 |

TABLE 1-continued

| | E Quotient | D Quotient | C Quotient | B Quotient | A Quotient |
|---|---|---|---|---|---|
| 1.3 | 0.9 | 1.0 | 0.5 | 0.1 | 0.9 |
| 2.3 | 1.1 | 0.9 | 0.3 | 0.1 | 1.1 |
| 8.3 | 1.7 | 0.6 | 1.1 | 1.4 | 8.5 |
| 9.3 | 1.5 | 1.1 | 1.0 | 1.3 | −12.1 |
| 10.3 | 0.8 | 0.5 | 0.5 | 0.6 | −3.1 |
| 16.3 | 1.0 | 0.9 | 0.7 | 0.1 | 0.9 |
| M2 | 0.5 | 1.2 | 0.4 | 0.8 | −3.9 |

Example 2

Another test was performed, identical to the test setup of Example 1, where a product according to an embodiment of the invention was used instead of an ordinary radiation protection product. The extending panel 3 had the following measures; distance f of the product was 60 mm and the angle, a, was 36 degrees, see FIG. 3b. The results when exposing a phantom head according to Example 1 and FIG. 4 is shown in Table 2 below.

Table 2 below illustrates the quotient between the radiation exposures for a user wearing the ordinary thyroid collar, according to Example 2, compared to not having any protection according to the set-up of Example 2. The values in Table 2 are the quotients in each position, as illustrated in FIGS. 4 and 5, in sections A-E, as illustrated in FIG. 6. Quotients of 1.0 and above indicates that no decrease in radiation was measured, whereas quotiens below 0 indicates that 100% radiation decrease was measured. Quotients inbetween 0 and 1 indicates a radiation decrease corresponding to the indicated value.

TABLE 2

| | E Quotient | D Quotient | C Quotient | B Quotient | A Quotient |
|---|---|---|---|---|---|
| 1.1 | 0.9 | 0.7 | 1.0 | 0.1 | 0.8 |
| 9.1 | 1.3 | 1.3 | 1.9 | 1.0 | −1.5 |
| 1.2 | 1.0 | 0.8 | 0.9 | 0.1 | 0.5 |
| 1.3 | 1.1 | 1.0 | 0.8 | 0.1 | 0.9 |
| 2.3 | 1.1 | 0.9 | 0.6 | 0.1 | 1.3 |
| 8.3 | 1.0 | 0.6 | 0.6 | 2.1 | 0.6 |
| 9.3 | 0.7 | 0.7 | 0.2 | 2.4 | 1.9 |
| 10.3 | 1.2 | 0.8 | 0.5 | 0.9 | −0.1 |
| 16.3 | 1.1 | 0.8 | 0.8 | 0.1 | 0.9 |
| M2 | 0.9 | 0.6 | 0.6 | 0.7 | 1.7 |

It is noted that the dosimeters record reduced radiation in those areas where the extension panel shields the dosimeters, thus the geometrical illustration in FIG. 3a and FIG. 3b corresponds well with the results from radiation exposure using phantom studies. Moreover the results from Example 2 vs Example 1 show that the use of an extension panel is beneficial to the wearer upon protection of the head and brain from harmful radiation coming from underneath.

Example 3

In a further Example, the efficacy of an ordinary protective collar design according to prior art, as illustrated in FIG. 3a, is demonstrated. The thyroid collar had a standard size. The thyroid collar was made from a woven radiation protection material with a safety level of 0.5 mmPb. A physician-phantom was set up in a clinical operating room equipped with a Siemens Artis Q (Siemens Healthineers, Germany) angio system and a Philips Multi Diagnost Eleva FD (Koninklijke Philips Electronics N.V) to simulate a clinical situation during an image-guided surgical intervention. A c-arm angular position with the physician-phantom placed frontal (zero degrees) towards the patient operation table, with an under-table X-ray tube position, and with the imaged area of the patient-phantom at the left side, in front of the physician-phantom. The patient phantom was placed on the table 80 cm above the floor and the height of the patient-phantom in the central beam was 21 cm. The zoom format was 48, SID was 125 cm, 2 frames per second, using 93 kV and 25.5 mAs and was filtered with 1 mm Al plus 0.1 mm Cu.

Table 3 below illustrates the quotient between the radiation exposures for a user wearing the ordinary thyroid collar, according to Example 3, compared to not having any protection according to the set-up of Example 3. The values in Table 3 are the quotients in each position in, as illustrated in FIGS. 4 and 5, in sections A-E, as illustrated in FIG. 6.

TABLE 3

| | E Quotient | D Quotient | C Quotient | B Quotient | A Quotient |
|---|---|---|---|---|---|
| 1.1 | 0.10 | 0.06 | 0.06 | 0.15 | 0.97 |
| 2.1 | 0.03 | 0.11 | 0.00 | 0.07 | 0.97 |
| 3.1 | 0.09 | 0.05 | 0.11 | 0.17 | 0.88 |
| 4.1 | 0.03 | 0.09 | 0.04 | 0.32 | 0.80 |
| 9.1 | 0.25 | 0.19 | 0.66 | 0.72 | 0.58 |
| 1.3 | 0.07 | 0.00 | 0.10 | 0.50 | 0.96 |
| 2.3 | 0.00 | 0.04 | 0.00 | 0.44 | 0.93 |
| 3.3 | 0.08 | 0.04 | 0.09 | 0.63 | 0.80 |
| 4.3 | 0.11 | 0.11 | 0.15 | 0.86 | 0.80 |
| 8.3 | 0.00 | 0.29 | 0.70 | 0.85 | 0.59 |
| 10.3 | 0.00 | 0.43 | 0.64 | 0.82 | 0.38 |
| 11.3 | 0.00 | 0.31 | 0.73 | 0.87 | 0.70 |
| 16.3 | 0.00 | 0.01 | 0.01 | 0.73 | 0.91 |
| M2 | 0.00 | 0.21 | 0.48 | 0.92 | 0.71 |

It is noted that an ordinary thyroid collar as used in Example 3 is efficient in section A of the phantom head as well as in the posterior part of section B, whereas it has no to low efficacy in the anterior section of section B and no to low efficacy in the sections C-E.

Example 4

Example 4 illustrates the efficacy of a radiation protective device, that may be used as a thyroid thyroid collar, for protection against radiation, such as ionizing radiation. The radiation protective device comprised a first section extending in a transverse direction, from a first front portion to a first back portion, in a coronal direction, and in a sagittal direction, the first front portion and the first back portion having a length in the coronal direction. Also, the radiation protective device comprised, a second section extending in the transverse direction, from a second front portion to a second back portion, in the coronal direction, and in the sagittal direction, the second front portion and the second back portion having a length in the coronal direction, wherein the second front portion of the second section is arranged at least partially coronal of the first front portion of the first section. An embodiment of the radiation protective device used in Example 4 is illustrated in FIG. 3b.

The radiation protective device was made from a woven radiation protection material with a safety level of 0.5 mmPb. The test setup in Example 4 was identical to Example 3. The panel 3 had the following measures; distance f of the product was 60 mm and angle a was 36 degrees. The results when exposing a phantom head according to Example 4 and at the positions and slices illustrated in FIGS. 4 and 6, respectively, is shown in Table 4 below.

Table 4 below illustrates the radiation exposure for a user wearing a thyroid collar according to Example 4 and the number is the measured reduction of radiation in each position as displayed in FIG. 4 compared to a phantom setup with no protection.

Table 4 below illustrates the quotient between the radiation exposures for a user wearing the radiation protective device according to Example 4 compared to not having any protection. The values in Table 4 are the quotients in each position in, as illustrated in FIGS. 4 and 5, in sections A-E, as illustrated in FIG. 6.

TABLE 4

|      | E Quotient | D Quotient | C Quotient | B Quotient | A Quotient |
|------|------------|------------|------------|------------|------------|
| 1.1  | 0.05       | 0.17       | 0.84       | 0.95       | 0.97       |
| 2.1  | 0.12       | 0.19       | 0.73       | 0.94       | 0.97       |
| 3.1  | 0.25       | 0.08       | 0.51       | 0.94       | 0.90       |
| 4.1  | 0.12       | 0.15       | 0.46       | 0.95       | 0.86       |
| 9.1  | 0.58       | 0.32       | 0.55       | 0.83       | 0.62       |
| 1.3  | 0.32       | 0.20       | 0.84       | 0.96       | 0.95       |
| 2.3  | 0.17       | 0.18       | 0.81       | 0.87       | 0.89       |
| 3.3  | 0.17       | 0.08       | 0.75       | 0.96       | 0.84       |
| 4.3  | 0.23       | 0.24       | 0.75       | 0.94       | 0.83       |
| 8.3  | 0.23       | 0.46       | 0.69       | 0.82       | 0.59       |
| 10.3 | 0.32       | 0.38       | 0.69       | 0.80       | 0.56       |
| 11.3 | 0.37       | 0.48       | 0.76       | 0.94       | 0.21       |
| 16.3 | 0.20       | 0.54       | 0.78       | 0.92       | 0.91       |
| M2   | 0.35       | 0.53       | 0.86       | 0.94       | 0.03       |

The results show that a thyroid collar with a panel according to Example 4 has high efficacy of reducing radiation dose in sections A-C whereas it has efficacy in the posterior part of section D. There is no to low efficacy of the anterior part of section E.

Comparing Example 3 and Embodiments

When comparing the results from using an ordinary thyroid collar according to Example 3 and the results from wearing a radiation protective device with a panel according to embodiments of the invention, as exemplified in Example 4, it can be concluded that the radiation reduction is greater for a radiation protective device with a second section extending in the transverse direction, from a second front portion to a second back portion, in the coronal direction, and in the sagittal direction, the second front portion and the second back portion having a length in the coronal direction, wherein the second front portion of the second section is arranged at least partially coronal of the first front portion of the first section, at least in sections B, C, and D. In Example 4, a radiation protective device with a specific size and shape of the second section was used. Other embodiments described herein will provide similar enhancements over the thyroid collar used in Example 3. The actual improvement in each section and for each embodiment will depend on the size and shape of the specific embodiment.

There are products on the market protecting a user's head and cranium from radiation coming from underneath, such as a lead reinforced glass shield or a protective cap with radiation protective panels extending from the cap down to cover the chin. Although those technical solutions are protecting the cranium from radiation, they are heavy and are supported by the head which means an increased risk for work related injuries in the neck. With the proposed solution, the additional weight is lower but also supported by the torso thus minimizing the risk for injuries.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules or segments. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

The present invention has been described above with reference to specific embodiments. However, other embodiments than the above described are equally possible within the scope of the invention. Different method steps than those described above may be provided within the scope of the invention. The different features and steps of the invention may be combined in other combinations than those described. The scope of the invention is only limited by the appended patent claims.

The invention claimed is:

1. A wearable radiation protective device for protection of the wearer against radiation, including ionizing radiation, comprising:
   a radiation protective first section extending in a transverse direction, from a first front portion to a first back portion, in a coronal direction, and in a sagittal direction, the first front portion and the first back portion having a length in the coronal direction; and
   a radiation protective second section extending in the transverse direction, from a second front portion to a second back portion, in the coronal direction, and in the sagittal direction, the second front portion and the second back portion having a length in the coronal direction, wherein the second front portion of the second section is arranged at least partially coronal of the first front portion of the first section;
   wherein the second front portion is configured with sufficient size to position an edge at and in front of the wearer's face between the chin and mouth with the first section positioned around the wearer's neck,
   wherein the edge is an upper and outer terminal edge of the radiation protective device.

2. The radiation protective device according to claim 1, wherein the second section is angled in the coronal direction relative the first section.

3. The radiation protective device according to claim 1, wherein the second section is radiation shielding material including a highly filled composition of one or more metals formed in one or more layers of metal combinations, and formed as a homogeneous casted film or fibrous material with fibers in regular or irregular patterns.

4. The radiation protective device according to claim 3, wherein the second section has an upper outer edge that is curved from a center of the second front portion towards the second back portion on each side, and a height of the second portion along the upper outer edge is higher at the front than at the back.

5. A radiation protective panel for protection of a wearer against radiation, including ionizing radiation, wherein the radiation protective panel is attachable to a radiation protective garment positionable around the wearer's neck and supported by the wearer, wherein said panel comprises a fastening mechanism configured to attach the protective panel reversibly or irreversibly to the protective garment, wherein the panel is curved or curveable to extend partially around the wearer's neck when attached to the radiation protective garment, wherein the panel is configured with sufficient size to position an edge at and in front of the wearer's face between the chin and mouth with the garment positioned around the wearer's neck, and wherein the edge is an upper and outer terminal edge of the radiation protective panel.

6. The radiation protective panel of claim 5, wherein the protective panel has a shape of a portion of a conical frustum wherein the smaller radius end of the conical frustum portion joins with a collar portion and said upper protective portion extends therefrom in anterior and lateral upward and outward directions.

7. The radiation protective panel of claim 6, wherein the protective panel is configured to extend cranially from the radiation protective garment coronally at about 45 degrees to a sagittal plane through the protective device.

8. The radiation protective panel of claim 7, wherein the protective panel has a plurality of slant heights with a longest slant height being at a center portion of the protective panel and wherein the longest slant height is from about 15 mm to about 150 mm.

9. The radiation protective panel of claim 5, wherein the protective panel is configured to be attached to protective garments comprising thyroid collars and aprons, and wherein said protective panel is one of a highly filled composition of one or more metals formed in one or more layers of metal combinations, or formed as a homogeneous casted film or fibrous material with fibers in regular or irregular patterns.

10. The radiation protective panel of claim 5, wherein the fastening mechanism comprises hook and loop fastening.

11. The radiation protective panel of claim 5, wherein the fastening mechanism comprises tape.

12. A wearable radiation protective device configured to protect at least the wearer's thyroid and brain from scattered radiation reflected from a patient positioned in front of the wearer, said device comprising:
a collar portion formed of a radiation shielding material configured to extend around the wearer's neck; and
an upper protective portion formed of a radiation shielding material having a shape of a portion of a conical frustum wherein the smaller radius end of the conical frustum portion joins with the collar portion and said upper protective portion extends therefrom in anterior and lateral upward and outward directions, wherein the upper protective portion is configured with sufficient size to position an edge at and in front of the wearer's face between the chin and mouth with the collar portion positioned around the wearer's neck, and wherein the edge is an upper and outer terminal edge of the radiation protective device.

13. The radiation protective device according to claim 12, wherein the upper protective portion is configured to extend coronally from the collar portion at an angle of about 45 degrees to a sagittal plane through the collar portion.

14. The radiation protective device according to claim 13, wherein the collar portion is a thyroid collar.

15. The radiation protective device according to claim 13, wherein the upper protective portion has a plurality of slant heights with a longest slant height being at a center portion of the upper protective portion and wherein the longest slant height greater than about 15 mm and less than about 150 mm.

16. The radiation protective device according to claim 15, wherein the longest slant height is greater than about 30 mm.

17. The radiation protective device according to claim 12, further comprising a lower portion formed of a radiation shielding material extending generally caudally from a front of the collar portion.

18. The radiation protective device according to claim 17, wherein the lower portion comprises a bib-like extension or an apron.

19. The radiation protective device according to claim 12, wherein the radiation shielding material comprises at least one of a filled composition of one or more metals, one or more layers of metal combinations, homogeneous casted film or fibrous material with fibers in regular or irregular patterns.

20. The radiation protective device according to claim 12, wherein the protective device comprises a thyroid collar or an apron.

* * * * *